(12) United States Patent
Dotta

(10) Patent No.: US 6,855,861 B2
(45) Date of Patent: Feb. 15, 2005

(54) PATCH WITH A FAST-OPENING PACKAGE, AND METHOD OF AND DEVICE FOR MANUFACTURING THE PACKAGE

(76) Inventor: Angelo Dotta, Via Alamandini, No. 10-40136 Bologna (IT)

( * ) Notice: Subject to any disclaimer, the term of this patent is extended or adjusted under 35 U.S.C. 154(b) by 0 days.

(21) Appl. No.: 10/223,110

(22) Filed: Aug. 15, 2002

(65) Prior Publication Data

US 2002/0198482 A1 Dec. 26, 2002

Related U.S. Application Data

(63) Continuation of application No. PCT/EP01/01555, filed on Feb. 13, 2001.

(30) Foreign Application Priority Data

Feb. 18, 2000 (IT) ..................................... TO2000A0156

(51) Int. Cl.[7] ........................... A61F 13/00; A61B 17/06
(52) U.S. Cl. ........................... 602/57; 602/54; 206/440; 206/441
(58) Field of Search ..................... 602/41–43, 54–59; 206/440, 441

(56) References Cited

U.S. PATENT DOCUMENTS

| | | | |
|---|---|---|---|
| 3,245,855 A | | 4/1966 | Stenvall |
| 3,630,201 A | * | 12/1971 | Endres .................. 604/390 |
| 4,235,337 A | * | 11/1980 | Dotta .................... 206/441 |
| 4,265,234 A | | 5/1981 | Schaar |
| 4,781,293 A | * | 11/1988 | Johns .................... 206/441 |
| 4,806,300 A | | 2/1989 | Walton et al. |
| 5,115,913 A | | 5/1992 | Anhauser et al. |
| 5,188,124 A | | 2/1993 | Feret |
| 5,333,753 A | * | 8/1994 | Etheredge ................ 221/33 |
| 5,397,297 A | | 3/1995 | Hunter |
| 5,505,306 A | | 4/1996 | Akemi et al. |
| 5,722,943 A | | 3/1998 | Sessions |

FOREIGN PATENT DOCUMENTS

| | | |
|---|---|---|
| EP | 0 635 262 | 1/1995 |
| EP | 0 810 078 | 12/1997 |

\* cited by examiner

*Primary Examiner*—Kim M. Lewis
(74) *Attorney, Agent, or Firm*—Katten Muchin Zavis Rosenman

(57) ABSTRACT

A patch with a fast-opening package comprises an adhesive support, possibly lacking the bandage pad and covered by one or more films of a protective material that can be separated from the adhesive support, a wrapper enclosing the patch and consisting of two half-wrappers that can be separated by pulling two end portions, at least one of the two half-wrappers being anchored to the one or more films protective material. At least one film of protective material has an extension that covers at least half the support and has a region submitted to die pressing to reduce the surface in contact with the adhesive, thereby allowing removal of the film by pulling the associated half-wrapper without a noticeable effort.

10 Claims, 2 Drawing Sheets

PATCH WITH A FAST-OPENING PACKAGE, AND METHOD OF AND DEVICE FOR MANUFACTURING THE PACKAGE

This application is a continuation of PCT EP01/01555, filed Feb. 13, 2001.

The present invention relates to a patch with a fast-opening package and to the means for manufacturing the package.

A known type of patch comprises an adhesive support onto which a gauze pad may be secured, usually in such a position that the pad is wholly surrounded by the adhesive support.

According to the prior art, the patches are enclosed within a paper package or wrapper keeping the sterility and adhesion properties of the patches until the moment they are applied.

Moreover, a film of protective material, generally of silicone paper, divided into two parts, is inserted between the gauze pad and the adhesive support.

Enhanced protective films with distinctive qualities are already known; as an example, a protective film characterised by the presence of an unevenness which keeps the wrapper away from the protective film thus avoiding that some liquid oozing out from the patch adheres to the wrapper is described in EP 0,635,262. Such an unevenness can be formed by die pressing, making the protective film to pass between two rotating rolls engraved with suitable pattern, as described in U.S. Pat. No. 5,188,124.

Packages for adhesive bandages that are opened by pulling the opposite ends of their wrappers are already known and industrially manufactured.

Said wrappers can be divided into two parts or half-wrappers or half-packages that allow exposing half the adhesive support and the gauze when being opened. The other half support is exposed by subsequently stripping, still by pulling, the remaining half-wrapper, as disclosed for instance in U.S. Pat. No. 4,235,337 to Dotta.

The opening capability of the wrapper is ensured in that the two separable half-wrappers are respectively anchored to a corresponding one of the two protective films of the adhesive bandage, and in that the anchoring area is located in correspondence with the area occupied by the gauze pad. Thus, being the initial film portions isolated from the adhesive by the gauze pad, stripping and folding of the protective films is made easier.

Without that measure, detaching the conventional protective films of silicone paper would be almost impossible, since the same films would be wholly engaged by the adhesive even in the areas.

It is an object of the present invention to allow a quick opening also for patches lacking a gauze or bandage pad and consisting of the only adhesive support, such as transdermal patches, or for patches having an adhesive bandage area, such as for instance hydro-colloid patches, or yet in all cases where the reduced size of the bandage pad scarcely isolates the protective material in the patch from the adhesive (e.g. adhesive bandages of the kind known as "Island dressings", cosmetical patches, and so on).

It is another object of the present invention to allow a quick opening in patches of the above mentioned kind by using, as protective material, the conventional silicone paper or the like, with planar shape, that is obtained by recovering the liner removed from the adhesive support, which liner protects the adhesive support before the gauze pad is applied during the patch manufacture.

According to the invention, the above and other objects are achieved as claimed in the appended claims.

The features of the invention and the advantages it affords will become apparent from the following description of preferred embodiments, shown only by way of non limiting example in the accompanying drawings, in which.

Figure 1:
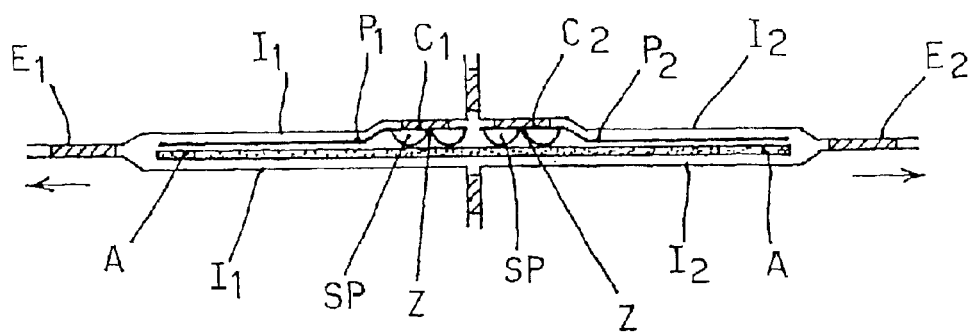
FIG. 1 is a schematical cross sectional view of a patch in a package according to a first embodiment of the invention.

Turning to FIG. 1, a cross-sectional view is shown of a package for a patch lacking a bandage pad and consisting of adhesive support A only. Protective films $P_1$ and $P_2$ are provided onto adhesive support A and the patch is enclosed inside a wrapper comprising half-wrappers $I_1$ and $I_2$ that can be separated by pulling opposite ends $E_1$ and $E_2$.

Films $P_1$ and $P_2$ have, in correspondence with regions $C_1$ and $C_2$ where they are glued to half-wrappers $I_1$ and $I_2$, a portion Z provided with hemispherical projections SP (with a diameter of about 2 mm) directed towards the adhesive surface of support A.

By pulling ends $E_1$ and $E_2$ of the package, half-wrappers $I_1$ and $I_2$ will tend to become separated and will draw with them, alternately, film $P_1$ or film $P_2$, the simultaneous detachment of both films $P_1$ and $P_2$ being highly improbable.

The detachment of films $P_1$ or $P_2$ from adhesive support A when the package is opened is allowed by projections SP, which act so that the area actually in contact with the adhesive is greatly reduced.

The effort required for removing said films $P_1$ and $P_2$ is thus greatly reduced if compared to the case when films $P_1$ and $P_2$ contact the adhesive of support A according to plane surfaces, in correspondence with gluing areas $C_1$ and $C_2$.

Projections SP are obtained by submitting a portion of the protective films to an alteration during patch manufacture, e.g. by die pressing. In the considered instance the alteration is an embossing, which provides an effective and cheap solution to the problem of reducing the surface in contact with the adhesive and moreover increases the film thickness.

Figure 2:
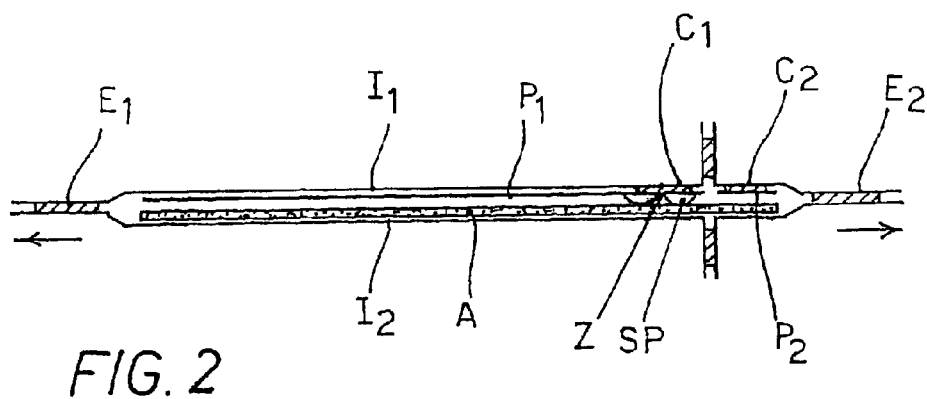
FIG. 2 is a schematical cross sectional view of a patch in a package according to a second embodiment of the invention.

Turning now to FIG. 2, a possible variant embodiment of the invention is shown, always in case of a patch lacking the bandage pad.

In the patch shown in FIG. 2, film $P_1$ has such an extension as to cover up to about 90% the adhesive support and has a set of projections SP in correspondence with gluing area $C_1$, whereas film $P_2$ lacks such projections.

Consequently, by exerting a pulling action on opposite package ends $E_1$ and $E_2$, preferential detachment of film $P_1$, together with half-wrapper $I_1$, is obtained first, since detachment of film $P_1$ is made easier by the provision of projections SP. The detachment of film $P_2$ can occur subsequently without appreciable effort, by acting on the side of film $P_2$ that remained free (the left-hand side in FIG. 2).

By exerting a pulling action in opposite directions on support A and end $E_2$, film $P_2$, being free at its left-hand side and being joined to half-wrapper $I_2$ at $C_2$, will undergo a torsion together with adhesive support A. Consequently, the exerted pulling action will no longer be applied to film $P_2$ in a direction parallel to the resting plane of film $P_2$ onto the underlying adhesive and, once a certain degree of torsion has been reached, film $P_2$ will become readily detached, together with $I_2$, from adhesive support A.

The arrangement shown in FIG. 2 can therefore allow a preferential opening of the package in a predetermined direction, by exposing most of the patch, always on one side and not on the other side. The same effect could be achieved also with a less pronounced differentiation of the films if compared with the arrangement shown in FIG. 2, for instance by sizing the protective films and the respective half-wrappers to a 2:1 ratio and by enhancing the projections provided on $P_1$ with respect to projections provided in this case also on $P_2$, so that $P_2$ exhibits a greater resistance to removal.

Figure 3:
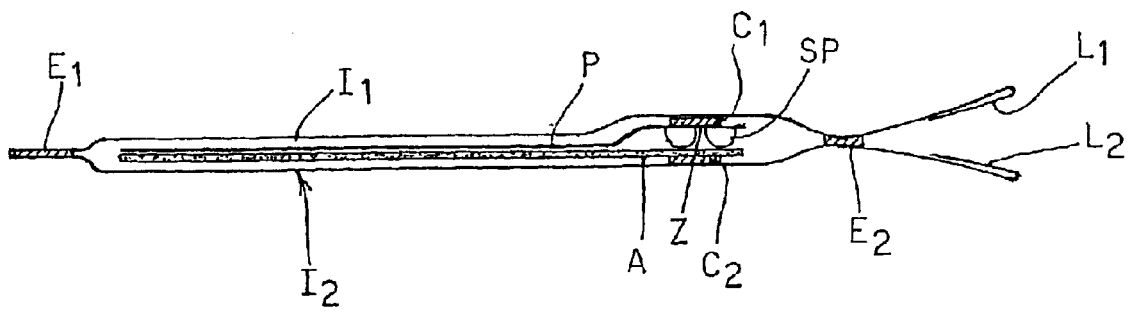
FIG. 3 is a schematical cross sectional view of a patch in a package according to a third embodiment of the invention.

An opening in a predetermined direction resulting in exposing even the whole patch is instead provided in the example shown in FIG. 3, always with reference to a patch lacking a bandage pad, this being the condition where opening is more difficult.

Support A, protected by film P, is enclosed inside a wrapper comprising facing half-wrappers $I_1$, $I_2$ that can be separated, or better peeled away, by pulling adjacent ends or tongues $L_1$, $L_2$. Preferably that wrapper, like the wrappers provided in the arrangements shown in FIGS. 1 and 2, is made of cold self-sealing paper or plastics or of paper or plastics thermo-weldable at moderate temperature and pressure, so that separation of the wrapper components does not require severe efforts or jerks.

In the embodiment shown in FIG. 3, the end of the back of adhesive support A close to tongues $L_1$, $L_2$ is joined with half-wrapper $I_2$ by gluing the inner surface of $I_2$ and the non-adhesive surface of patch A at area $C_2$, said gluing being preferably obtained by spreading an adhesive over $I_2$.

The end of film P close to tongues $L_1$, $L_2$ is joined with half-wrapper $I_1$ by gluing at area $C_1$, where projections SP are also provided that are directed towards the adhesive in support A and that considerably reduce the area actually in contact with the adhesive itself. Conversely, thanks to the gluing at $C_2$, patch A remains glued by its back to half-wrapper $I_2$, which can be handled to make the patch adhere to the skin without even touching the patch itself by the fingers. Once the patch has been made to adhere, the user will strip off half-wrapper $I_2$, and the back of patch A will not exhibit noticeable traces of the adhesive spread over $I_2$ at area $C_2$. Moreover, gluing at $C_2$ will prevail without difficulty over the adhesive of support A, thereby keeping the back thereof attached to half-wrapper $I_2$, still thanks to projections SP reducing the contact area between P and A.

Figure 4:
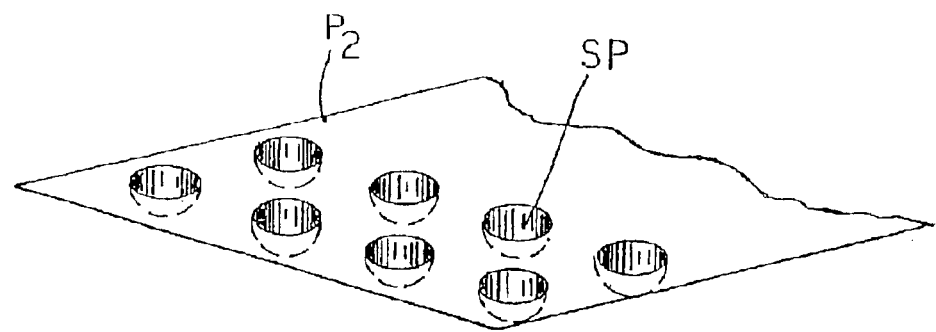
FIG. 4 is an enlarged view of a portion of protective material.

Turning to FIG. 4, hemispherical projections SP are preferably made by embossing and are arranged in parallel rows put close to each other and staggered in a honeycomb pattern.

Figure 5:
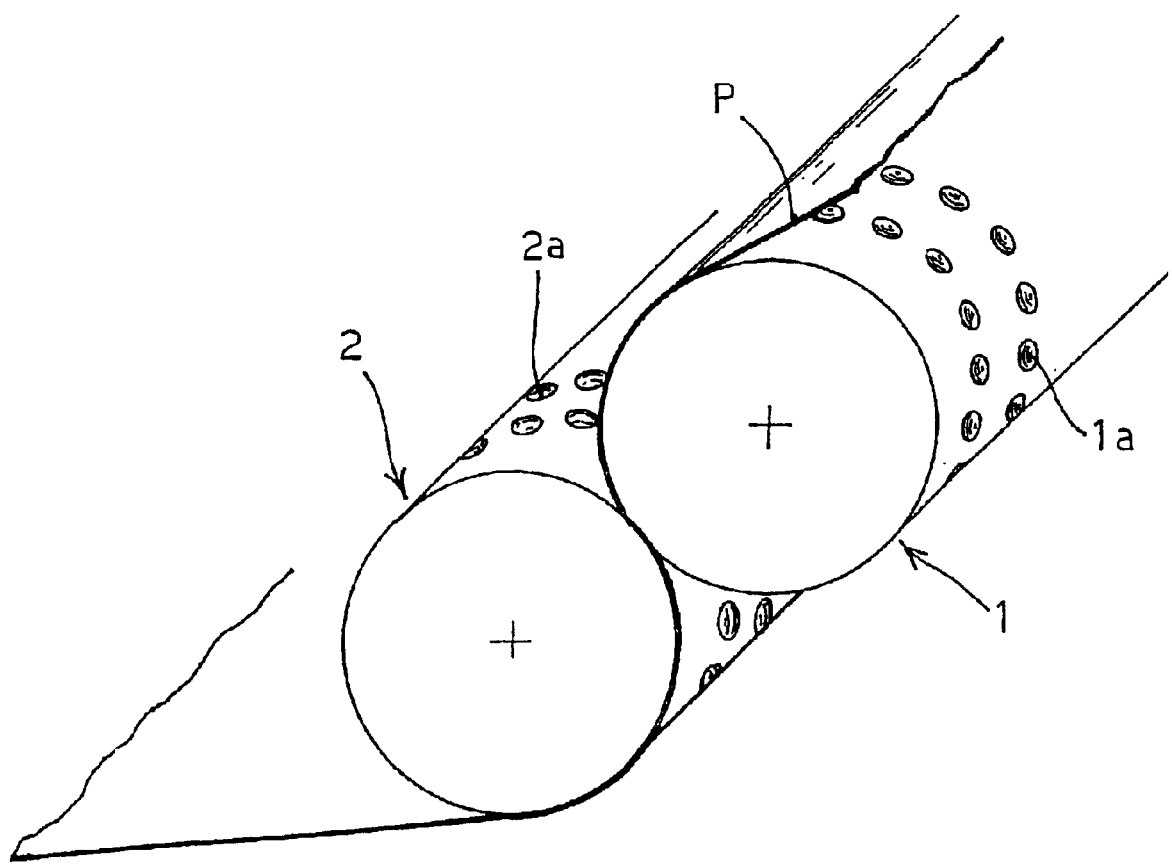
FIG. 5 is a schematical view of the device for die pressing the protective material.

Turning now to FIG. 5, a device for die pressing the protective material is schematically shown. In FIG. 5, reference 1 denotes a rotating female cylindrical die and reference 2 denotes a corresponding rotating male die. Said dies 1 and 2 co-operate with each other and are equipped with projections 1a and complementary recesses 2a between which protective material P to be die pressed is made to pass.

Advantageously, protective material P to be embossed can be submitted to a treatment by which it is made more flexible and/or robust in order to reduce lesions and/or crushing due to the die pressing operation. That treatment includes for instance localised application, before or after die pressing, of suitable plastic materials, preferably by spraying or by cold or hot spreading.

With reference to the die pressing, it is to be appreciated that it can result in concave areas—instead of convex areas—directed towards the adhesive, or in mere lacks of materials, e.g. holes. The essential feature is that the surface contacting the adhesive is reduced and, possibly, that the film thickness is increased.

Even if the invention has been disclosed with reference to a patch lacking a bandage pad, it can be employed with advantage also in case of patches equipped with said pads.

What is claimed is:

1. A patch with a fast-opening package, comprising:
   an adhesive support covered by one or more films of a protective material that is separable from said adhesive support, at least one of said films having an extension that covers at least half the surface of the adhesive support; and
   a wrapper enclosing said adhesive support and substantially consisting of two half-wrappers that are separated by pulling two end portions, at least one of said two half-wrappers being anchored to said protective material,
   wherein said one or more films has, on the side in contact with the adhesive and in correspondence with an anchoring region where said one or more films is anchored to said half-wrappers, a portion provided with a plurality of projections or recesses that reduce the surface of the protective film in contact with the adhesive, said portion being limited to said anchoring region thereby allowing removal of the one or more films by pulling the associated half-wrapper without such an effort as to deform the adhesive support forming the patch or to cause detachment of the film from the associated half-wrapper.

2. A patch as claimed in claim 1, wherein said adhesive support is protected by a single protective film and is enclosed inside a wrapper consisting of two facing plane half-wrappers that are welded together along their edges and that are separable by pulling two respective projecting adjacent ends defining a pair of tongues, said single protective film being anchored to the associated half-wrapper, and the back of the adhesive support opposite to said single protective film being anchored to the other half-wrapper, the anchoring regions being located near the edge of the adhesive support directed towards said tongues for the wrapper opening.

3. A patch as claimed in claim 1, wherein the adhesive support is protected by at least two films and is enclosed inside a wrapper substantially consisting of two half-wrappers shaped as envelopes with facing open sides that are joined to each other but that are separable by pulling their respective opposite end portions.

4. A patch as claimed in claim 1, wherein the adhesive support is protected by at least two protective films and is enclosed inside a wrapper substantially consisting of two half-wrappers shaped as envelopes with facing open sides that are joined to each other but that are separable by pulling their respective opposite end portions, a first one of said protective films comprising on the side in contact with the adhesive support and in correspondence with the anchoring regions, a portion provided with a plurality of projections or recesses that reduce the surface of the protective films in contact with the adhesive support, whereas the other one of said protective films is lacking said plurality of projections or recesses and has a reduced length compared to the first one of said protective films, whereby said second film is foldable within its half-wrapper, after removal of the first protective film, until becoming detached from said adhesive support.

5. A patch as claimed in claim 1, wherein said projections are hemispherical projections directed towards an adhesive surface of said adhesive support.

6. A patch as claimed in claim 5, wherein said hemispherical projections are arranged in several rows located close to each other and staggered in a honeycomb pattern.

7. A patch as claimed in claim 1, wherein said projections or recesses increase the film thickness, thereby allowing removal of the film by pulling the associated half-wrapper without such an effort as to deform the adhesive support forming the patch or to cause detachment of the film from the associated half-wrapper.

8. A patch as claimed in claim 1, wherein said projections or recesses are obtained by means of embossing.

9. A patch as claimed in claim 1, further comprising a gauze or bandage secured onto said adhesive support.

10. A patch as claimed in claim 1, wherein said at least one film of protective material is obtained from conventional silicone paper with planar shape, recovered from a liner removed from the adhesive support, which liner protects the adhesive support before the gauze pad is applied during the patch manufacture.

* * * * *